United States Patent [19]

Pattison et al.

[11] 4,069,340

[45] Jan. 17, 1978

[54] IMMONIUM SALTS AND DERIVATIVES THEREOF

[75] Inventors: Victor A. Pattison, Clarence Center; Russell L. K. Carr, Grand Island, both of N.Y.

[73] Assignee: Hooker Chemicals & Plastics Corporation, Niagara Falls, N.Y.

[21] Appl. No.: 661,681

[22] Filed: Feb. 26, 1976

Related U.S. Application Data

[63] Continuation-in-part of Ser. No. 653,694, Jan. 30, 1976, abandoned, which is a continuation of Ser. No. 663,897, Aug. 28, 1967, abandoned.

[51] Int. Cl.² .......................................... C07C 119/00
[52] U.S. Cl. .................................... 424/298; 424/325; 260/453 A; 260/619 R; 260/619 D; 260/620; 260/621 R; 260/621 M; 260/622 R; 260/622 P; 260/623 R; 260/623 D; 260/624 R

[58] Field of Search ..................... 260/453 R, 566 R; 424/325, 298

[56] References Cited

U.S. PATENT DOCUMENTS

3,404,208  10/1968  Robertson et al. .................. 260/566

*Primary Examiner*—Gerald A. Schwartz
*Attorney, Agent, or Firm*—Peter F. Casella; William J. Crossetta, Jr.; Arthur S. Cookfair

[57] ABSTRACT

There are provided: novel aryloxy immonium salts, prepared by the reaction of their corresponding haloformates with amides; and phenolic compositions corresponding to the aryloxy immonium salts. These novel aryloxy immonium salts and their corresponding phenolic compositions have utility as chemical intermediates, antioxidants, stabilizers and antibacterials.

13 Claims, No Drawings

IMMONIUM SALTS AND DERIVATIVES THEREOF

This is a continuation-in-part of Ser. No. 653,694, filed Jan. 30, 1976, now abandoned which is a continuation of Ser. No. 663,897, filed Aug. 28, 1967, now abandoned.

This invention relates to novel compounds, their preparation and uses as chemical intermediates, antioxidants, stabilizers and antibacterials.

More particularly, it relates to the preparation of a novel and unusual class of immonium salts and their utility as chemical intermediates in reactions to produce phenolic compositions.

It is an object of this invention to provide novel immonium salts and processes for preparing them.

Another object of this invention is to prepare aryloxy substituted immonium salts.

A further object of the invention is to provide novel immonium salts useful as chemical intermediates, antioxidants, stabilizers and antibacterials.

An additional object of this invention is to provide phenolic compositions derived from the novel immonium salts of this invention, which compositions are useful as antioxidants, stabilizers and antibacterials.

Another object of this invention is to provide novel processes for preparing phenolic compositions utilizing the novel immonium salts of this invention as chemical intermediates.

Still further objects and the scope of the present invention will become apparent from the detailed description given. It should be understood, however, that the detailed description and specific examples, while indicating preferred embodiments of the invention, are given by way of illustration only, since various changes and modifications within the spirit and scope of the invention will become apparent from this description to those skilled in the art.

In accordance with this invention, immonium salts have been prepared of the general formula:

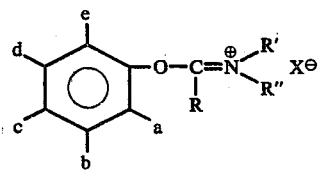
(I)

wherein $a$, $b$, $c$, $d$, and $e$ are independently selected from the group consisting of hydrogen, hydrocarbyl, α-haloalkyl, halogen and nitro; R is selected from the group consisting of hydrogen, alkyl and aryl; R' and R" are independently selected from the group consisting of hydrogen and alkyl, preferably of 1 to 12 carbon atoms, and X is selected from the group consisting of bromine, chlorine and fluorine; the hydrocarbyl groups and α-haloalkyl are of from one to thirty carbon atoms, and preferably of 1 to 12 carbon atoms, and most preferably of 1 to 6 carbon atoms, and aryl is selected from the group phenyl and naphthyl.

By the term hydrocarbyl is meant the radical obtained by removal of one hydrogen atom from a hydrocarbon and thus encompasses alkyl, alkenyl, aryl, cycloalkyl, cycloalkenyl, alkylaryl and arylalkyl.

All of the above described radicals encompass hydrocarbon radicals of from about one to about thirty carbon atoms, with the term aryl encompassing benzene and naphthalene radicals. The above radicals are more fully described here by definite examples.

This invention also includes the process of preparing compositions of formula (I) which comprises reacting compositions having the formula:

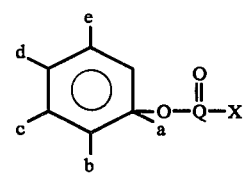
(II)

with compositions of the formula:

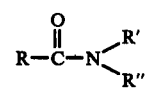
(III)

wherein $a$, $b$, $c$, $d$, $e$, R, R', R", and X are as above described, and Q is selected from the group consisting of carbon and sulfur.

The preparation of the novel immonium salts of this invention is illustrated by the following general equation:

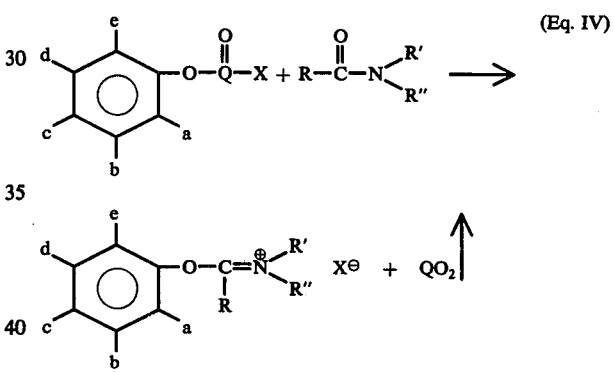
(Eq. IV)

The above equation (IV) illustrates the novel process of this invention, wherein aryl haloformates in reaction with amides or substituted amides form the novel aryloxy substituted immonium salts of this invention, together with carbon dioxide or sulfur dioxide. When the evolution of chlorine dioxide or sulfur dioxide has substantially ceased, a substantially pure product is formed. In a more restricted fashion, this invention includes preferred novel compositions of the following general formula:

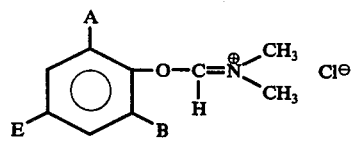
(V)

wherein A, B, and E are independently selected from the group consisting of hydrogen, alkyl, and α-haloalkyl, the alkyl and α-haloalkyl groups being from one to thirty carbon atoms, but preferably of 1 to 12 carbon atoms, and most preferably of 1 to 6 carbon atoms.

The present process for preparing compositions of Formula (V) comprises reacting a haloformate composition of the formula:

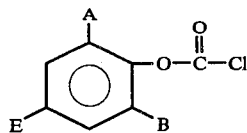

(VI)

with dimethyl formamide wherein A, B, and E are as above described.

Used as chemical intermediates, the instant novel compounds of this invention of formula (I) participate in the process for preparing phenolic compositions of formula:

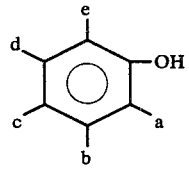

(VII)

which comprises reacting compositions of Formula (I) with substantially equimolar quantities of compositions of formula GOH, wherein $a$, $b$, $c$, $d$, $e$, R, R', R", and X are as defined above; and G is selected from the group hydrogen and lower alkyl of 1 to 6 carbon atoms.

Another novel process for preparing compositions of Formula (VII) comprises reacting compositions of Formula (II) with dihydrocarbyl sulfoxides such as dimethyl sulfoxide and the like.

Thus, the novel process for preparing phenolic compositions of Formula (VII), which comprises reacting the novel compositions of Formula (I) used as chemical intermediates, is illustrated by the following general equation:

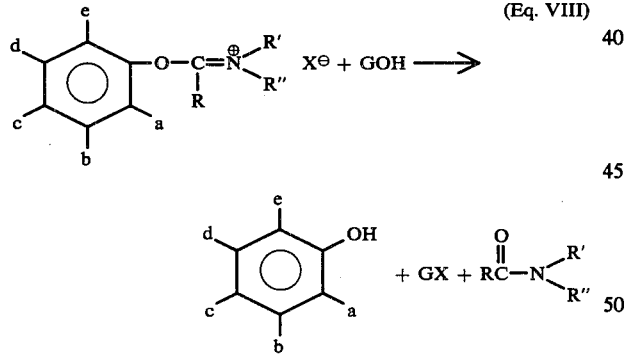

(Eq. VIII)

It is seen from the above Equation (VIII) that GOH, being water or a lower alkanol, reacts with compositions of Formula (I) to form compositions of Formula (VII), hydrogen halide or alkyl halide, and the corresponding amide.

In the above Equation (VIII), the reactants are utilized in stoichiometric, less than, or greater than the stoichiometric proportions to effect the novel compositions of formula (VII).

Thus, in the above Equation (VIII) the composition GOH may be used at 0.1 to 100 times the stoichiometric proportions, more preferably at 0.3 to 10 times, although approximately stoichiometric proportions are most preferred. Such excesses or deficiencies may also be employed in the other reactions recited in this specification, wherein stoichiometric proportions are preferred.

In another aspect, this invention includes a process for preparing phenolic compositions of formula:

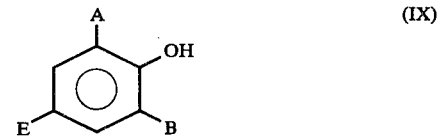

(IX)

by reacting compositions of Formula (V) with equimolar quantities of methanol wherein A, B, and E are as described. With reference to the preparation of the phenolic compositions of Formula (IX) or (VII) above, less than or greater than equimolar quantities of reagent GOH may be used, although stoichiometric quantities are preferred. It is obvious that if less than equimolar quantities of reagent GOH are used, decreased quantities of the above described phenolic compositions are produced.

The present invention also includes the process for preparing phenolic compositions of formula:

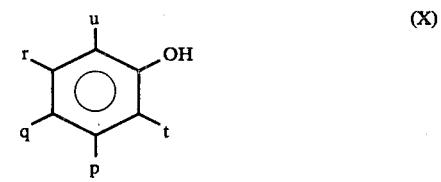

(X)

wherein at least one of the group $t$, $p$, $q$, $r$, and $u$ is J—CH$_2$—and wherein $t$, $p$, $q$, $r$, and $u$ are selected from the group consisting of hydrogen, hydrocarbyl, alkyl, α-haloalkyl, halogen, nitro, and J—CH$_2$-, wherein the nucleophile J- is selected from the group consisting of alkoxy, cyano, dialkylphosphono, bis(alkylcarbonyl), amino, alkylthio, and nitrato, and wherein the sum of the J—CH$_2$—'s is from one to two, which comprises reacting compositions of Formula (VII), wherein $a$, $b$, $c$, $d$, and $e$ are independently selected from the group consisting of hydrogen, hydrocarbyl, alkyl, haloalkyl, halogen, and nitro, where the sum of the α-haloalkyls is from one to two, and the number of α-haloalkyls is equal to the number of J—CH$_2$—'s in the phenolic composition of Formula (X), with a nucleophilic reagent of formula J-D wherein J-D is selected from the nucleophile group of water, alkanols, alkali metal cyanides, trialkyl phosphites, alkanediones, amines, mercaptans, and silver nitrate.

The novel process for preparing phenolic compositions of Formula (X) thus includes a reaction of the nucleophilic reagent of Formula J-D with the α-haloalkyl group of the phenolic compositions of Formula (VII). A specific example of this novel process is illustrated in Equation (XI) below, which illustrates the process for preparing p-methoxymethyl phenol which comprises reacting p-chloromethyl phenol with methanol.

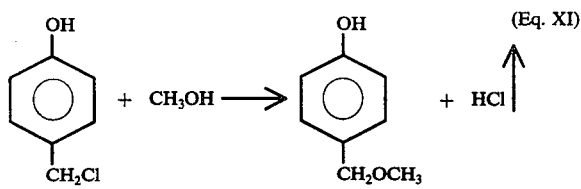

(Eq. XI)

The novel process of this invention for preparing phenolic compositions of Formula (X) may also be effected by consecutive reactions starting with compositions of Formula (I) or with the haloformates of Formula (II).

Thus, one of the preferred processes of this invention comprises the novel reaction of a starting haloalkyl aryl haloformate or halosulfite Formula (II) with one mole of an amide Formula (III) to produce an in situ novel immonium salt Formula (I). This immonium salt is then subsequently reacted with a composition GOH (described above) to form in situ an intermediate phenolic composition Formula (VII). The intermediate phenolic composition of Formula (VII) is then subsequently reacted with a nucleophile of formula J-D described above to effect the final J—CH$_2$— substituted phenolic composition, wherein the sum of the J—CH$_2$—'s is one or two.

One of the preferred processes of the invention thus comprises the following steps:

1. The α-halomethyl aromatic haloformate (as a chloromethyl phenyl chloroformate) and an equivalent amount (sometimes less or greater than an equivalent amount is used) of an amide (often dimethyl formamide) were reacted by stirring in a suitable solvent (as acetonitrile) for a suitable period to finish the reaction (often about an hour). The amide used as a reactant in a suitable solvent may be used in the range of 0.1 to 100 times the stoichiometric proportion, more preferably at 0.3 to 10 times, although approximately stoichiometric proportions are most preferred.

In some cases, however, the amide may serve as a reaction solvent in which it then may be used in excess in the range of 1.1 to 1000 times the stoichiometric proportion, more preferably at 3 to 100 times, although approximately 5 to 50 times the stoichiometric proportions are most preferred.

The time of reaction may vary from 5 minutes to 48 hours, more preferably from 30 minutes to 24 hours, although approximately ½ to 2 hours are preferred. The temperature of this step may vary from the freezing point to the boiling point of the solvent, but ambient temperatures are preferred. The most preferred temperature range is from 25°–30° C. The solvent here may be any solvent such as acetonitrile, benzene, toluene, cyclohexane, propionitrile, and the like which will effect solution of the reaction ingredients without participating in the reaction. Acetonitrile is often the preferred solvent.

2. The above prepared immonium salt (which may be isolated if desired) was treated with an equivalent amount (sometimes less or greater than an equivalent amount is used) of composition GOH (methanol often preferred) and the mixture was stirred for a suitable period (often one hour) to prepare the corresponding phenolic composition. The temperature + time preferences of Step 1 are retained for Step 2. The amount of GOH wherein GOH is used as a reactant in a suitable solvent (described in Step 1) follows exactly the amide preferences of Step 1.

The term "excess" in the following table for CH$_3$OH refers to the use of GOH as a reaction solvent and the amide reaction solvent preferences of Step 1 are retained.

3. The above prepared phenolic composition was treated with an equivalent amount (sometimes less or greater than an equivalent amount is used) of a nucleophile, and the reaction mixture was stirred and/or heated to effect reaction. The amount of nucleophile wherein the nucleophile is used as a reactant in a suitable solvent (described in Step 1) follows exactly the amide preferences of Step 1.

The term "excess" in the following table under nucleophile refers to the use of excess nucleophile as a reaction solvent and the amide reaction preferences of Step 1 are retained. The final nucleophile substituted phenolic composition may be isolated by suitable means as illustrated in the examples. The temperature ranges here may vary from the freezing point to the boiling point of the reaction mixture, but temperatures in the range of ambient to reflux are preferred. The reaction time preferences of Step 1 are retained for Step 3.

The table below summarizes some of the effected embodiments of this invention - reactions of the chloromethylphenols. Similar reactions are effected if other corresponding haloalkyl haloformates are used.

In the table below on reactions of chloromethylphenols the numbers indicate the molar ratio of the reagent of the starting material, but often a greater or smaller molar ratio may be used if desired as described above in the preferred ranges.

The triethyl amine in the second example of this table is not a true nucleophile here but merely an HCl acceptor.

The term DMF in the following table refers to dimethyl formamide.

| Starting Material | Reactions of Chloromethylphenols | | | | % Yield |
|---|---|---|---|---|---|
| | DMF | CH$_3$OH | Nucleophile | Product | |
| ClCH$_2$—⌬—O—C(O)Cl | 1.0 | excess | excess CH$_3$OH | CH$_3$OCH$_2$—⌬—OH | 85 |
| ClCH$_2$—⌬—O—C(O)Cl | 1.0 | 1.0 | 1.0(CH$_3$C(O))$_2$CH$_2$ [1.0(C$_2$H$_5$)$_3$N] | (CH$_3$C(O))$_2$CHCH$_2$—⌬—OH | 78 |

Reactions of Chloromethylphenols

| Starting Material | DMF | CH₃OH | Nucleophile | Product | % Yield |
|---|---|---|---|---|---|
| 4-ClCH₂-phenyl-O-C(O)Cl | 1.0 | excess | 1.0 NaCN | 4-(N≡CCH₂)-phenol | 45 |
| 4-ClCH₂-phenyl-O-C(O)Cl | 1.0 | 1.0 | 1.0 (C₂H₅O)₃P | 4-[(C₂H₅O)₂P(O)-CH₂]-phenol | 93 |
| 2-ClCH₂-phenyl-O-C(O)Cl | 1.0 | excess | excess CH₃OH | 2-(CH₂OCH₃)-phenol | Fair |
| 2-ClCH₂-phenyl-O-C(O)Cl | 1.0 | excess | 1.0 NaCN | 2-(CH₂-C≡N)-phenol | 83 |
| 2-ClCH₂-phenyl-O-C(O)Cl | 1.0 | excess | 1.0 (C₂H₅O)₃P | 2-[CH₂P(O)(OC₂H₅)₂]-phenol | 99 |
| 3-CH₃-2-(O-C(O)Cl)-6-CH₂Cl benzene | 2.0 | 1.0 | 1.0 (C₂H₅O)₃P | 3-CH₃-2-OH-6-[CH₂P(O)(OC₂H₅)₂] benzene | 74 |
| 2,6-bis(CH₂Cl)-phenyl-O-C(O)Cl | 2.0 | 1.0 | 2.5 (C₂H₅O)₃P | cyclic phosphonate: 2-[CH₂-P(OC₂H₅)₂]-6-CH₂- benzo-dioxaphosphole | Fair |

The above described nucleophilic reagent of formula J-D may also be selected from the nucleophile group of silver nitrate, mercaptans, and amines.

Using silver nitrate as an embodiment of a nucleophile in reaction with the α-haloalkylaryls of Formula (VII), wherein the sum of the α-haloalkyls is selected from the group one and two, produces the corresponding α-nitratoalkylaryl phenolic composition of Formula (X).

In accordance with the above, the use of mercaptan as a nucleophile results in the corresponding α-alkylthiomethylene aryl phenolic composition.

Also in accordance with the above, the use of amines or ammonia as the nucleophile effects the corrresponding α-amino alkyl aryl phenolic composition where the amino radical is selected from the group —$NR_hR'_h$ and ±$NR_hR'_hR''_h$ wherein $R_h$, $R'_h$, and $R''_h$ are independently selected from the group of hydrogen, alkyl, aryl, and hydrocarbyl. The carbon atom preferences for the hydrocarbyl group of Formula (I) are retained.

The starting haloformates of this invention embraced by Formula (II) can be prepared, for example, by phosgenation of the appropriate phenol. The α-haloalkyl haloformates are prepared by free radical chlorination of the above prepared haloformate with phosphorus trichloride, sulfuryl chloride, benzamide, and benzoyl peroxide. Examples 1 through 4 give illustrations of the preparations of the starting haloformates.

Typical examples of suitable haloformates embraced by Formula (II), or more restrictedly, by Formula (VI), include phenyl chloroformate, p-cresyl chloroformate, 2,6 xylyl chloroformate, 2-chloro-p-cresyl chloroformate, α-chloro-2,6-xylyl chloroformate, m-cresyl chloroformate, m-cresyl bromoformate, o-cresyl chloroformate, o-cresyl bromoformate, p-chloromethyl-phenyl chloroformate, m-chloromethyl-phenyl chloroformate, o-chloromethyl-phenyl chloroformate, o-chloromethyl-phenyl bromoformate, 2,6-dichloromethyl-phenyl bromoformate, phenyl bromoformate, m-cresyl fluoroformate, p-bromomethyl-phenyl chloroformate, m-bromomethyl phenyl chloroformate, o-bromomethyl-phenyl chloroformate, 3,5-xylyl chloroformate, 3,5-xylyl bromoformate; α,α' dichloro-3,5-xylyl chloroformate; α, α'-dibromo-3,5-xylyl chloroformate; α,α'-dibromo-3,5-xylyl bromoformate; 3,4-xylyl chloroformate; α,α'-dichloro-3,4-xylyl chloroformate; α,α'- dibromo-3,4-xylyl bromoformate, p-chloro-o-benzyl chloroformate; 3,5-diisopropylphenyl chloroformate, α-chloro-3,5-diisopropyl chloroformate, α-bromo-3,5-diisopropylphenyl chloroformate, 2-allylphenyl chloroformate, 2-(2,3-dichloropropyl)phenyl chloroformate and 2-(2,3-dibromopropyl)phenyl bromoformate and mixtures thereof. Typical examples of suitable halosulfites of this invention embraced by Formula (II) include phenyl chlorosulfite, o-cresyl chlorosulfite, examples formed by replacing carbon in the listing of haloformates above with sulfur to form the corresponding halosulfites, and mixtures thereof.

Suitable amides for this invention include compositions having the Formula III which include dimethyl formamide, dimethyl acetamide, formamide, acetamide, propionamide, n-butyramide, isobutyramide, stearamide, benzamide, nicotinamide, acetanilide, acetophenetidine, benzanilide, urethane, urea, carbanilide, N-ethyl-2-naphthamide, N,N-dimethyl acetamide, p-toluanilide, benzo-p-toluidide, pentadecanamide, 4-methyl-2-pentenamide, cyclo hexane carboxamide, melanamide, 2-acetamide quinoline, 4-benzamido pyridine, 4-butyeryl morpholine, α-valerolactam, and mixtures thereof.

The immonium salts of this invention include those of the general Formula (I) and the more specific Formula (V).

Typical examples of suitable aryloxy-substituted immonium salts include the immonium salt of dimethyl formamide and α-chloro-p-cresyl chloroformate, the immonium salt of dimethyl formamide and p-cresyl chloroformate; the immonium salt of dimethyl formamide and α,α'-dichloro-2,6-xylyl chloroformate; the immonium salt of dimethyl formamide and o-cresyl chloroformate; the immonium salt of dimethyl formamide and p-chloro-o-benzyl chloroformate and m-cresyl chloroformate, the immonium salt of dimethyl formamide and α-chloro-o-cresyl chloroformate; the immonium salt of dimethyl formamide and α-chloro-m-cresyl chloroformate; the immonium salt of dimethyl acetamide and α,α'-dibromo-2,6-xylyl bromoformate and mixtures thereof.

Other suitable examples of aryloxy-substituted immonium salts include all the examples formed by any combination of a compound selected from the list of the haloformates or halosulfites in combination with a compound selected from the list of the amides and mixtures thereof.

Typical examples of the phenolic compositions embraced by general Formula (VII) and the more specific Formula (IX) include the following: p-chloromethyl phenol, m-chloromethyl phenol, o-chloromethyl phenol, p-bromomethyl phenol, 2-methyl-6-chloromethyl phenol, 2-methyl-6-bromomethyl phenol, 2,6-dichloromethyl phenol, p-chloro-o-benzyl phenol, 2,6-dibromomethyl phenol, 2,6-difluoromethyl phenol, o-cresol, m-cresol, p-cresol, 2,6-xylenol and mixtures thereof.

Other typical examples of suitable phenolic compositions of general Formula (VII) may be derived from the list of the haloformates by substituting the phenolic hydroxyl group for the haloformate group and mixtures thereof.

Typical examples of compositions of Formula GOH described above in the formation of phenolic compositions of Formula (VII) include water, deuterium oxide and the lower alkanols, where G is selected from the group hydrogen and lower alkyl, and lower alkyl may be more specifically defined as containing from one to six carbon atoms. Thus, typical examples included in the group of lower alkanols include methanol, ethanol, propyl alcohol, isopropyl alcohol, butyl alcohol, isobutyl alcohol, amyl alcohol, isoamyl alcohol, hexyl alcohol, isohexyl alcohol, t-butyl alcohol, hexanol-2 and mixtures thereof.

Typical examples of nucleophilic reagents of general Formula J-D used in the preparation of phenolic compositions of general Formula (X) are selected from the group of alkanols, alkali metal cyanides, mercaptans, silver nitrate, trialkyl phosphites, amines and alkanediones.

The alkanols of general formula ROH, where R has the carbon atom preferences of the hydrocarbyl radical of Formula (I), include the above mentioned lower alcohols and other alcohols such as octanol, decanol, isodecanol, lauryl alcohol, stearyl alcohol and mixtures thereof.

The alkali metal cyanides are included in the group lithium cyanide, sodium cyanide, potassium cyanide, rubidium cyanide and cesium cyanide.

Typical examples of suitable trialkyl phosphites include phosphites of general Formula $(RO)_3P$, wherein R has the carbon atom preferences of the hydrocarbyl radical of Formula (I), and suitable examples include trimethyl phosphite, triethyl phosphite, tripropyl phosphite, tributyl phosphite, diethylmethyl phosphite, trihexyl phosphite, dibutyldecyl phosphite, trinonyl phosphite and mixtures thereof.

Typical examples of alkanediones include more specifically the group of $\alpha,\alpha$-diketones which include acetyl acetone, 2,4-pentanedione, 2,4-hexanedione, 2,4-octanedione and mixtures thereof.

Typical examples of suitable nucleophilic amines include, in addition to ammonia, methylamine, dimethylamine, trimethylamine, ethylamine, diethylamine, triethylamine, dipropylamine, isopropylamine, allylamine, diallylamine, dibutylamine, isobutylamine, sec-butylamine, t-butylamine, amylamine, cyclohexylamine, dicyclohexylamine, 2-aminoheptane, 2-amino-4-methylhexane, decylamine, dioctylamine, trioctadecylamine, tallow amine and mixtures thereof.

Typical examples of suitable nucleophyl mercaptans include the entities where sulfur is substituted for the oxygen of the alkanols. In addition, suitable mercaptans include methyl mercaptan, ethyl mercaptan, propyl mercaptan, butyl mercaptan, amyl mercaptan, hexyl mercaptan, heptyl mercaptan, octyl mercaptan, nonyl mercaptan, 2-mercapto-ethanol, 2,3-dimercapto-1-propanol and mixtures thereof.

Typical examples of suitable silver nitrate type nucleophile compounds include silver nitrate and other soluble salts of group Ib of the periodic table which form insoluble metal halides, especially insoluble metal chlorides, and mixtures thereof.

Numerous examples of the novel aryloxy substituted immonium salts of this invention may be obtained from any combination of the above listed haloformates and the above listed amides.

The above synthesized compositions of Formula (I) may be utilized to synthesize suitable products of Formula (VII) by reaction of the above compositions of Formula (I) with compositions of Formula GOH, described above.

The synthesized compositions of Formula (VII) may be utilized to synthesize compositions of Formula (X) by reaction of the compositions of Formula VII with the above described examples of nucleophilic reagents of Formula J-D.

It is noteworthy that processes of this invention enable one to prepare phenolic compositions which are often unstable when prepared by other synthetic methods.

Also novel and noteworthy is the application of our novel immonium salts as antioxidants, stabilizers, and antibacterials. These utilities also apply to the phenolic compositions derived from the novel immonium salts of this invention. Surprisingly, the immonium salts of this invention have utility not only because of their intrinsic chemical structure but also because of their slow atmospheric hydrolysis to their corresponding phenolic compositions. In this way, they are particularly effective in applications as antioxidants, stabilizers, and antibacterials. These utilities also apply to the phenolic compositions of Formula (VII), Formula (IX) and Formula (X). The phenolic compositions of Formula (VII), (IX), and (X) - and their corresponding immonium salt compositions are particularly effective antibacterials against Eberthella typhosa or Staphylococcus aureus. Most effective and preferred are the alkyl, halogen, and/or arylalkyl substituted phenolic compositions and their corresponding immonium salts.

For example, the immonium salt of dimethyl formamide and p-chloro-o-benzyl chloroformate can be particularly effective and preferred as a slow acting and excellent bactericide. This immonium salt used by itself or in solution, dispersion, or emulsion in a non-aqueous, aqueous/non-aqueous, unctuous, or essentially non-aqueous form will slowly hydrolyze when exposed to atmospheric moisture (or to a composition GOH, where G is selected from the group hydrogen and lower alkyl of 1 to 6 carbon atoms) to its corresponding phenol, p-chloro-o-benzyl phenol. This phenol is an excellent bactericide, having phenol coefficients in the order of 150–200 against Staphylococcus aureus and Eberthella typhosa.

It is especially noteworthy that the novel immonium salts of this invention-in particular those immonium salts corresponding to utilizable antibacterial phenolic compositions - will slowly hydrolyze or decompose to their corresponding efficacious phenolic composition with moderation of the irritating effect of the phenol on tissue; but with a slow, desirable, long lasting liberation of the antibacterial phenol.

Thus this invention also claims an antibacterial composition comprising an efficacious amount of the immonium salt of Formula (I) incorporated in a suitable vehicle.

To those skilled in the art it is obvious that the term "efficacious amount" depends on the utility involved, the vehicle, and the efficiency of the corresponding phenol; but, in general, the efficacious concentration of the immonium salt will correspond roughly to the known efficacious concentration of the corresponding phenol, since phenols are well established antibacterials. Thus antibacterial concentrations of 0.001 to 50% of the immonium salt in a suitable vehicle are possible - in addition to its application alone, but concentrations of 0.01 to 10% are preferred, with concentrations of 0.1 to 1% most preferred.

The term "suitable vehicle" can vary according to the utility involved, and includes organic solvents, soaps, powders, detergents, creams, oils, organic/water emulsions, unctuous bases - and other media dictated by the utility involved.

This invention also claims a method for the control of bacteria which comprises applying to the locus to be treated an antibacterial amount of the immonium salt of Formula (I).

It is preferred to employ a solvent or solvents during the instant novel processes of this invention; however no solvent, or an excess of one of the reagents may be employed if desired.

The following examples are presented to describe the invention more fully without any intent of being limited thereby. All parts and percentages are by weight, and all temperatures are in degrees centigrade unless otherwise specified.

EXAMPLE 1

PREPARATION OF p-CRESYL CHLOROFORMATE

A solution of 1100 parts of p-cresol in 4330 parts of toluene was cooled to $-10°$ and 1500 parts of phosgene was condensed therein. Sodium hydroxide solution (20%, 36.60 parts) was added slowly with stirring keeping the temperature $<0°$. The product layer was separated, washed with water, dried over sodium sulfate and the solvent removed by distillation. The product was distilled through a Vigreaux column to yield 1230 parts (71%) of product boiling at $97°-100°/14$ mm. of mercury $n_{25}{}^D = 1.5100$ (Nuclear magnetic resonance spectra confirmed the identity of the product).

EXAMPLE 2

PREPARATION OF 2,6 - XYLYL CHLOROFORMATE.

This material was prepared in the same manner as the p-cresyl chloroformate above using 373 parts of 2,6-xylenol and 483 parts of phosgene. Distillation yielded 448 parts (81%) of product boiling at $155°-157°/150$ mm. of mercury, $n_{25}{}^D = 1.5023$. Elemental analyses, infrared and nuclear magnetic resonance spectra confirmed the identity of the product.

EXAMPLE 3

PREPARATION OF α-CHLORO-p-CRESYL CHLOROFORMATE.

A mixture of 1110 parts of p-cresyl chloroformate, 23.1 parts of phosphorous trichloride and 2.3 parts benzamide was heated to 135°. The temperature was controlled at that point while a mixture of 12.3 parts of benzoyl peroxide and 995 parts of sulfuryl chloride was added over a period of six hours to the stirred reaction. When addition was complete the liquid residue was distilled through a Vigreaux column yielding 885 parts (66%) of solid product boiling at $127°-130°/4.5$ mm. of mercury; m.p. $60.5°-61.5°$. Elemental analyses, infrared and nuclear magnetic resonance spectra confirmed the identity of the product.

EXAMPLE 4

PREPARATION OF α-CHLORO-2,6 XYLYL CHLOROFORMATE AND α,α'-DICHLORO-2,6-XYLYL CHLOROFORMATE

A mixture of 420 parts of 2,6-xylyl chloroformate, 17 parts of phosphorus trichloride and 1.7 parts of benzamide was reacted at 135° over a period of six hours with a mixture of 7 parts of benzoyl peroxide and 740 parts of sulfuryl chloride. The liquid residue was carefully distilled through a helix packed column. This yielded two major fractions. One fraction boils at 135°–145°/10 mm. of mercury and yielded 125 parts (25%) of α-chloro-2,6-xylyl chloroformate; $n_{25}{}^D = 1.5310$. Elemental analyses, infrared and nuclear magnetic resonance spectra confirmed the identity of the product.

A second fraction boiled at 162°–165°/10 mm. of mercury and yielded 143 parts (25%) of α,α'-dichloro-2,6-xylyl chloroformate as a white solid melting at 71.5°–73.5°. Elemental analyses, infrared spectra, and nuclear magnetic resonance spectra confirmed the identity of the product.

EXAMPLE 5

PREPARATION OF THE IMMONIUM SALT OF DIMETHYL FORMAMIDE AND α-CHLORO-p-CRESYL CHLOROFORMATE

A mixture of 10.2 parts of α-chloro-p-cresyl chloroformate and 47 parts of dimethyl formamide was stirred for one half hour. There was a vigorous reaction, gas evolved, and an orange precipitate formed. The precipitate was quickly filtered into a Soxhlet extractor and was extracted for four hours with anhydrous ether. The solid was then poured into acetonitrile and the residual solid collected by suction filtration in the absence of air. After drying, the material was a light colored hygroscopic solid. Elemental analyses agreed with $C_{10}H_{13}Cl_2NO$, while infrared and nuclear magnetic resonance spectra confirmed the identity of the product.

EXAMPLE 6

PREPARATION OF THE IMMONIUM SALT OF DIMETHYL FORMAMIDE AND p-CRESYL CHLOROFORMATE

The process of Example 5 was repeated using p-cresyl chloroformate in the same molar proportion as α-chloro-p-cresyl chloroformate.

Nuclear magnetic resonance spectra confirmed the identity of the product.

EXAMPLE 7

PREPARATION OF THE IMMONIUM SALT OF DIMETHYL FORMAMIDE AND α,α'-DICHLORO-2,6-XYLYL CHLOROFORMATE

The process of Example 5 was repeated using α,α'-dichloro-2,6-xylyl chloroformate in the same molar proportions as α-chloro-p-cresyl chloroformate. The corresponding immonium salt was obtained in good yield.

EXAMPLE 8

PREPARATION OF THE IMMONIUM SALT OF DIMETHYL FORMAMIDE AND o-CRESYL CHLOROFORMATE

The process of Example 5 was repeated using o-cresyl chloroformate in the same molar proportions as α-chloro-p-cresyl chloroformate. The corresponding immonium salt was obtained in good yield.

EXAMPLE 9

PREPARATION OF THE IMMONIUM SALT OF DIMETHYL FORMAMIDE AND m-CRESYL CHLOROFORMATE

The process of Example 5 was repeated using m-cresyl chloroformate in the same molar proportions as α-chloro-p-cresyl chloroformate. The corresponding immonium salt was obtained in good yield.

EXAMPLE 10

PREPARATION OF THE IMMONIUM SALT OF DIMETHYL FORMAMIDE AND α-CHLORO-o-CRESYL CHLOROFORMATE

The process of Example 5 was repeated using α-chloro-o-cresyl chloroformate. The corresponding immonium salt was obtained in good yield.

EXAMPLE 11

PREPARATION OF THE IMMONIUM SALT OF DIMETHYL FORMAMIDE AND α-CHLORO-m-CRESYL CHLOROFORMATE

The process of example 5 was repeated using α-chloro-m-cresyl chloroformate. The corresponding immonium salt was obtained in good yield.

EXAMPLE 12

PREPARATION OF p-CHLOROMETHYL PHENOL

Equimolar quantities of p-chloromethylphenyl chloroformate and dimethyl formamide were reacted at room temperature for one hour in acetonitrile (590 parts acetonitrile for every mole of dimethyl formamide or p-chloromethylphenyl chloroformate). Equimolar quantities of methanol were then added to the immonium salt mixture, and the solution was then stirred for about one half hour (with cooling) at 25°–30° C.

Nuclear magnetic resonance spectra confirmed the existence of p-chloro-methyl phenol in solution.

EXAMPLE 13

PREPARATION OF o-CHLOROMETHYL PHENOL

The process of Example 12 was followed using o-chloromethyl chloroformate in the same molar proportions as p-chloromethyl chloroformate.

The corresponding o-chloromethyl phenol was obtained in solution.

EXAMPLE 14

PREPARATION OF 2-METHYL-6-CHLOROMETHYL PHENOL

The process of Example 12 was followed, using 2-methyl-6-chloromethyl-phenyl chloroformate in the same molar proportions as p-chloromethyl chloroformate. The corresponding 2-methyl-6-chloromethyl phenol was obtained in solution.

EXAMPLE 15

PREPARATION OF 2,6-DICHLOROMETHYL PHENOL

The process of Example 12 was followed using 2,6-dichloromethyl phenyl chloroformate in the same molar proportions as p-chloromethyl chloroformate. The corresponding 2,6-dichloromethyl phenol was obtained in solution.

EXAMPLE 16

PREPARATION OF p-METHOXYMETHYL PHENOL

The process of Example 12 was repeated but in this case excess methanol (1000 g. of methanol/mole of the immonium salt) was added. The reaction mixture was stirred for one hour, diluted with water, and extracted with ether. After drying the product solution over sodium sulfate, evaporating the solvent, and trituration of the residue oil with hexane, p-methoxymethyl phenol was obtained in 78% yield, M.P. 79°–80°. Infrared and nuclear magnetic resonance spectra confirmed the identity of the product.

EXAMPLE 17
PREPARATION OF o-METHOXYMETHYL PHENOL

The process of Example 16 was essentially repeated using o-chloromethyl phenyl chloroformate in the same molar proportions as p-chloromethylphenyl chloroformate. The corresponding product, o-methoxymethyl phenol, was obtained after fractionation; b.p. 70°/3 mm. of mercury, $n_{23}^D$ 1.5355. Infrared and nuclear magnetic spectra confirmed the identity of the product.

EXAMPLE 18
PREPARATION OF 3(4'-HYDROXYBENZYL)-2,4-PENTANEDIONE

A solution of p-chloromethyl phenol in acetonitrile (Example 12) was reacted with equimolar dimethyl amine and equimolar 2,4-pentanedione by stirring together for 1 hour. The reactive mixture was diluted with water, acidified with hydrochloric acid, extracted with ether, and then the ether extract was dried with sodium sulfate. The residual oil was triturated with benzene to yield 78% of 3(4' hydroxybenzyl)-2,4-pentanedione, M.P. 93°–94.5° C. Infrared and nuclear magnetic resonance spectra confirmed the identity of the product.

EXAMPLE 19
PREPARATION OF α-CYANO-p-CRESOL

A solution of p-chloromethyl phenol in acetonitrile (Example 12) was reacted with equimolar sodium cyanide in excess methanol (800 parts methanol/mole sodium cyanide) and the reaction mixture was refluxed for one hour. The oil after solvent evaporation (washed as in Experiment 18) was fractionated to yield 45% of α-cyano-p-cresol (b.p. 150°–155°/1 mm. of mercury; M.P. 68°–70°). Infrared spectra confirmed the identity of the product.

EXAMPLE 20
PREPARATION OF α-CYANO-o-CRESOL

The process of Example 19 was repeated using o-chloromethyl phenol in the same molar proportions as p-chloromethyl phenol. Infrared spectra confirmed the identity of the product.

EXAMPLE 21
PREPARATION OF 4-DIETHYLPHOSPHONOMETHYL PHENOL

A solution of p-chloromethyl phenol in acetonitrile (Example 12) was reacted with equimolar ethyl phosphite at about 50°. When the exothermic reaction had ceased the solvent was removed by distillation and the pottemperature was raised to 175°. The product was dissolved in ether, washed with water, dried with sodium sulfate, and the solvent evaporated.

The product, 4-methylphosphonomethyl phenol, was obtained in 93% yield, M.P. 89°–91°.

The infrared and nuclear magnetic resonance spectra confirmed the identity of the product.

EXAMPLE 22
PREPARATION OF 2-DIETHYLPHOSPHONOMETHYL PHENOL

The process of Example 21 was repeated using o-chloromethyl phenol in the same molar proportions as p-chloromethylphenol.

The product was distilled in a molecular still (95°–170°/7µ) in 99% yield ($n_{25}^D$ 1.5150). Elemental analyses ($C_{11}H_{17}C_{14}P$), infrared spectra and nuclear magnetic resonance spectra confirmed the identity of the product.

EXAMPLE 23
PREPARATION OF 2-METHYL-o-DIETHYLPHOSPHONOMETHYL PHENOL

The process of Example 21 was repeated using 2-methyl-o-chloromethyl phenol in the same molar proportions as p-chloromethylphenol. The product (100°–125°/1µ) was obtained in 74% yield.

Elemental analyses ($C_{12}H_{19}O_4P$), infrared spectra, and nuclear magnetic resonance spectra confirmed the identity of the product.

EXAMPLE 24
PREPARATION OF 2-ETHOXY-2-OXO-7-DIETHYLPHOSPHONOMETHYL-4-5-BENZO-1-OXA-2-PHOSPHOLANE

The process of Example 21 was repeated using 2,6-dichloromethyl phenol in the same molar preparations as p-chloromethylphenol.

The product (165°–200°/1µ) was obtained in fair yield.

Elemental analyses ($C_{16}H_{22}P_2O_6$), infrared spectra and nuclear magnetic resonance spectra confirmed the identity of the product.

It is understood that the details provided in the foregoing specification can be modified by those skilled in the art without departing from the scope of the invention.

We claim
1. The compound of the formula

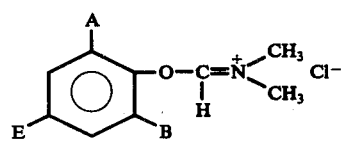

wherein A, B and E are independently selected from the group consisting of hydrogen, alkyl of 1 to 30 carbon atoms, and α-haloalkyl of 1 to 30 carbon atoms, wherein said halo is independently selected from the group consisting of chlorine, bromine and fluorine.

2. The compound according to claim 1 wherein A, B and E are independently selected from the group consisting of hydrogen, alkyl of 1–6 carbon atoms and α-haloalkyl of 1–6 carbon atoms.

3. The compound according to claim 1 of the formula

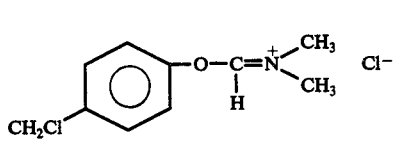

4. The compound according to claim 1 of the formula

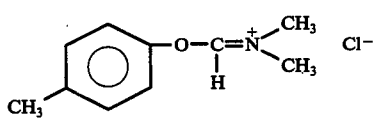

5. The compound according to claim 1 of the formula

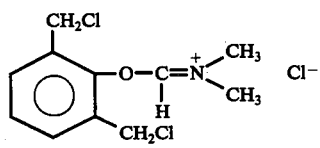

6. The compound according to claim 1 of the formula

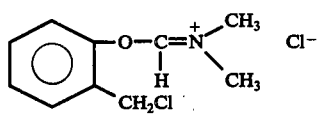

7. The compound according to claim 1 of the formula

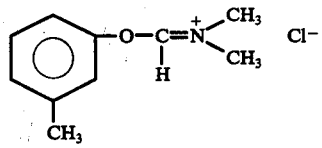

8. The compound of the formula

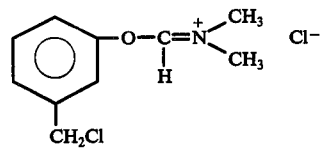

9. The compound of the formula

10. A process for preparing a compound of the formula

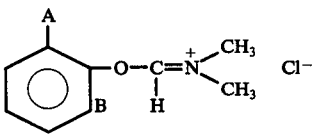

which comprises reacting dimethyl formamide with a compound of the formula

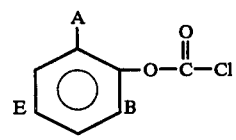

wherein A, B and E are independently selected from the group consisting of hydrogen, alkyl of 1 to 30 carbon atoms, and α-haloalkyl of 1 to 30 carbon atoms, wherein said halo is independently selected from the group consisting of chlorine, bromine, and fluorine.

11. A process according to claim 10 which comprises reacting dimethyl formamide with a compound of the formula

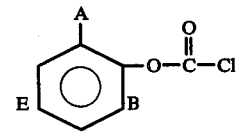

wherein A, E, and B are independently selected from the group consisting of hydrogen, alkyl of 1 to 6 carbon atoms and α-haloalkyl of 1 to 6 carbon atoms.

12. An antibacterial composition comprising

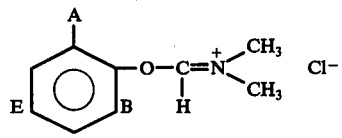

wherein A, E, and B are selected from the group consisting of hydrogen, alkyl of 1 to 30 carbon atoms and α-haloalkyl of 1 to 30 carbon atoms, wherein said halo is selected from the group consisting of chlorine, bromine and fluorine.

13. An antibacterial composition according to claim 12 wherein A, E, and B are selected from the group consisting of hydrogen, alkyl of 1 to 6 carbon atoms and α-haloalkyl of 1 to 6 carbon atoms.

* * * * *